US012426885B2

(12) United States Patent
Walzman

(10) Patent No.: US 12,426,885 B2
(45) Date of Patent: Sep. 30, 2025

(54) MESH CAP FOR AMELIORATING OUTPOUCHINGS

(71) Applicant: Daniel Ezra Walzman, Teaneck, NJ (US)

(72) Inventor: Daniel Ezra Walzman, Teaneck, NJ (US)

( * ) Notice: Subject to any disclaimer, the term of this patent is extended or adjusted under 35 U.S.C. 154(b) by 756 days.

(21) Appl. No.: 17/020,797

(22) Filed: Sep. 14, 2020

(65) Prior Publication Data

US 2020/0405347 A1 Dec. 31, 2020

Related U.S. Application Data

(63) Continuation-in-part of application No. 16/602,319, filed on Sep. 12, 2019, now Pat. No. 11,382,636, which is a continuation-in-part of application No. 16/024,639, filed on Jun. 29, 2018, now Pat. No. 10,617,428, which is a continuation of application (Continued)

(51) Int. Cl.
| | |
|---|---|
| *A61B 17/12* | (2006.01) |
| *A61L 29/14* | (2006.01) |
| *A61L 31/14* | (2006.01) |
| *A61B 17/00* | (2006.01) |
| *A61B 90/00* | (2016.01) |

(52) U.S. Cl.
CPC .. *A61B 17/12113* (2013.01); *A61B 17/12031* (2013.01); *A61B 17/1214* (2013.01); *A61B 17/12172* (2013.01); *A61B 17/12177* (2013.01); *A61B 17/1219* (2013.01); *A61L 29/145* (2013.01); *A61L 31/145* (2013.01); *A61L 31/146* (2013.01); *A61B 2017/00867* (2013.01); *A61B 2017/00898* (2013.01); *A61B 2017/1205* (2013.01); *A61B 2090/3966* (2016.02)

(58) Field of Classification Search
CPC ........ A61B 17/12113; A61B 17/12172; A61B 17/1214
See application file for complete search history.

(56) References Cited

U.S. PATENT DOCUMENTS

| | | |
|---|---|---|
| 3,874,388 A | 4/1975 | King et al. |
| 4,282,875 A | 8/1981 | Serbinenko |
| (Continued) | | |

FOREIGN PATENT DOCUMENTS

WO 2011/057002 A2 5/2011

*Primary Examiner* — Sarah A Long

(57) ABSTRACT

A self-expandable occluding device can both cover the neck of an outpouching and serve as a permanent embolic plug thereby immediately stabilizing the outpouching. The self-expandable device effectively covers the neck of an outpouching with, for example, a mesh, or other at least partially occluding component, in a desired orientation across the neck of the outpouching without projecting into the parent vessel. The device incorporates elements which immediately stabilize the device in the outpouching, in effect, functioning as a permanent embolic plug. An embolic disc is combined with retention arms of flexible material, which deploy within the outpouching and provide immediate stabilization thereby retaining the occluding component or mesh across the neck of the outpouching. In illustrative embodiments, the arms are in the form of coils configured to deploy into three dimensional structures.

46 Claims, 10 Drawing Sheets

Related U.S. Application Data

No. 15/732,519, filed on Nov. 20, 2017, now Pat. No. 10,543,015.

(60) Provisional application No. 62/600,134, filed on Feb. 13, 2017, provisional application No. 62/497,851, filed on Dec. 5, 2016.

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward, Jr. |
| 4,921,478 A | 5/1990 | Solano et al. |
| 5,165,421 A | 11/1992 | Fleischhacker et al. |
| 5,263,963 A | 11/1993 | Garrison et al. |
| 5,334,210 A | 8/1994 | Gianturco |
| 5,628,761 A | 5/1997 | Rizik |
| 5,733,294 A | 3/1998 | Forber et al. |
| 5,907,893 A | 6/1999 | Zadno-Azizi et al. |
| 6,221,086 B1 | 4/2001 | Forber |
| 6,375,670 B1 | 4/2002 | Greenhalgh |
| 6,605,102 B1 | 8/2003 | Mazzocchi et al. |
| 7,128,736 B1 * | 10/2006 | Abrams ............ A61B 17/0057 606/1 |
| 7,575,582 B2 | 8/2009 | Gandhi et al. |
| 2002/0173835 A1 | 11/2002 | Bourang et al. |
| 2004/0087998 A1 * | 5/2004 | Lee ................. A61B 17/12172 606/200 |
| 2004/0127935 A1 * | 7/2004 | VanTassel ............ A61F 2/0105 606/200 |
| 2005/0159645 A1 | 7/2005 | Bertolero et al. |
| 2006/0106421 A1 * | 5/2006 | Teoh ................ A61B 17/12022 606/213 |
| 2006/0293612 A1 | 12/2006 | Jenson et al. |
| 2007/0078480 A1 | 4/2007 | Belenkaya et al. |
| 2008/0033341 A1 | 2/2008 | Grad |
| 2010/0069948 A1 | 3/2010 | Veznedaroglu et al. |
| 2010/0087709 A1 | 4/2010 | Bertolero et al. |
| 2011/0144669 A1 | 6/2011 | Becking et al. |
| 2011/0152993 A1 | 6/2011 | Marchand et al. |
| 2013/0045182 A1 | 2/2013 | Gong et al. |
| 2015/0272589 A1 * | 10/2015 | Lorenzo ........... A61B 17/12145 606/200 |
| 2016/0022445 A1 * | 1/2016 | Ruvalcaba ....... A61B 17/12163 606/198 |
| 2019/0209178 A1 * | 7/2019 | Richter ............ A61B 17/12113 |
| 2020/0046370 A1 * | 2/2020 | Gorochow ....... A61B 17/12113 |

\* cited by examiner

MESH CAP FOR AMELIORATING OUTPOUCHINGS

TECHNICAL FIELD

The described disclosure relates generally to endovascular devices, and, more particularly, relates to a specifically shaped support cap atop a mesh disc.

BACKGROUND

The present disclosure is applicable to both gastrointestinal (GI) organs, vascular aneurysms and brain aneurysms. More specifically, the present disclosure is applicable in the repair of outpouchings, including both diverticulum and aneurysms. In illustrative embodiments, the present disclosure relates to an endovascular device for filling of a variety of vascular malformations, or other pathologic outpouchings. Outpouchings may include vascular aneurysms found in intracranial aneurysms, a fusiform aneurysm which is an outpouching of the arterial wall and a saccular aneurysm, which consists of a neck, a stem, and a dome.

Present procedures for ameliorating outpouchings including, vascular, cerebral, intestinal outpouchings, involve surgical clipping of the outpouching via an open procedure or via an interventional endovascular procedure. One other conventional procedure involves the placement of one or more coils within the outpouching or aneurysmal sac via a microcatheter. The primary limitation associated with vascular procedures is that "wide-necked" outpouchings (or aneurysms) are not generally amenable to this type of treatment due to the likelihood that the implanted devices may be subject to displacement within or from the aneurysm sac. Another limitation associated with procedures which use a single thread coil device is that the device usually requires the surgeon to pack the coil(s) within the aneurysm and thereby increasing the risk of damaging both the vessel and the aneurysm walls.

Additional current procedures also incorporate the use of a stent, for example, an intercranial stent, to function as a buttress to retain the coils within the aneurysmal sac, particularly in outpouchings or aneurysms exhibiting widenecked anatomies. This approach, however, may increase the potential of damage to surrounding blood vessels, and/or require antiplatelet therapy to prevent in-stent thrombosis which increases the potential for bleeding complications.

While the prior art discloses the use of self-expanding coils, these devices fail to provide a structure which decreases the permeability of blood across the neck of the outpouching, thus resulting in higher rates of coil compaction within the outpouching, and recurrence of the outpouching with its attendant risks. The present disclosure employs a surgical device including a mesh element, positioned predominantly across the neck of the aneurysm/out-pouching to overcome this limitation.

The prior art also discloses the use of hydrogel and/or hydrogel combined, particularly, in a vascular environment. The use of hydrogel in some instances may exacerbate medical difficulties due to uneven swelling of the hydrogel, adversely altering the delivery characteristics for the related mesh occluders and otherwise presenting difficulties for use in certain treatments.

SUMMARY

The present disclosure obviates the short comings of the prior art with the utilization of a mesh or occluding element, and associated components, that secure the position of the occluding element relative to an outpouching before detachment, and before and/or subsequent to placement of additional embolic materials including embolic coils. More specifically, the present disclosure comprises a self-expandable occluding device which can both cover the neck of the outpouching and serve as a permanent embolic plug thereby immediately stabilizing the outpouching. Moreover, the self-expandable device effectively covers the neck of an outpouching with, for example, a mesh, or other at least partially occluding component, in a desired orientation across the neck of the outpouching without projecting into the parent vessel. The device incorporates elements which immediately stabilize the device in the outpouching, in effect, functioning as a permanent embolic plug. In illustrative embodiments, the present disclosure combines an embolic disc with retention arms of flexible material, such as wire comprised of, for example, shape memory material including metals and polymers, super-elastic materials, spring material, etc. which deploy within the outpouching and provide immediate stabilization thereby retaining the occluding component or mesh across the neck of the outpouching. In illustrative embodiments, the arms are in the form of coils are configured to deploy into three dimensional structures.

In illustrative embodiments, the retention arms may be in the shape of a coil defining a structure which at least partially follows the contours of the inner area of the outpouching to stabilize, for example, immediately stabilize, the occluding disc or mesh adjacent the neck of the outpouching. The retention arms in the form of a coil or other configuration may be configured to engage or "grip" the inner wall of the outpouching, with the mesh or occluding element optimally positioned at the neck of the outpouching. The configuration of the retention arms may be in the form of one or more coil loops connected together to form a dome-shape structure or alternatively may be independent from each other. It is further contemplated that the retention arms may not necessarily form a coil-shape upon deployment but may be slightly curved orientation or even relative linear in orientation. In other illustrative embodiments, the one or more retention arms may inter-engage with one or more primary embolic coils, previously or subsequently introduced within the outpouching, to provide a further stabilizing or retaining structure within the outpouching. In an even further illustrative embodiment, the retention arms may engage with hydrogel injected within the outpouching or aneurysm, and cooperate with the hydrogel, to provide further supportive functions.

Briefly, and in general terms, the present disclosure provides a mesh occluder for treatment of an outpouching, and a system and method for deploying the mesh occluder from a parent vessel into the outpouching. In one aspect, the system includes an occluding component, for example, in the form of a mesh, that can at least partially or fully cover the neck of an outpouching. In certain embodiments, the mesh occluder establishes a permanent embolic plug in the outpouching. The mesh occluder may include one or more self-expanding components which provide a simple or unified complex matrix that expands as it is deployed and achieves multiple configurations including, and without limitation, a generally half-spherical or semi-ovoid configuration, or other shapes such as pyramidal, kidney-shaped, bi-lobed, or other complex shapes, so that the self-expandable outpouching-filling device can be secured promptly in its desired position within the outpouching. In other illustrative embodiments, the filling device includes retention arms which are slightly curved and/or linear, The optional configuration of the occluding component, for example, a mesh disc, of the mesh occluder of the present disclosure may have a single layer, or be multi-layered. Other, optional embodiments of the occluding component or mesh disc, include an opening through the occluding component, for example, generally centrally located, to permit introduction of an embolic material such as a hydrogel, gelfoam, ethanol, polyvinyl-alcohol particles, calibrated microspheres, central vascular plugs, coils, n-butyl-cyanoacrylate glue, fibrin glue, polidocanol-foam, alcoholic prolamin solution, and ethylene vinyl alcohol copolymer. The areas of the occluding element defining the opening may have its edges tapered or dimpled inward relative to the outpouching, to define a cone-like region to facilitate entry or re-entry of components, embolic fluid, etc. into the outpouching.

The mesh occluder may be a component of a medical system including a microcatheter and a delivery wire to which the mesh occluder is attached. The mesh occluder may be detachably connected to the delivery wire. In some illustrative embodiments, the distal end of the microcatheter can extend through the occluding component, for example, through the opening in the occluding component thereby providing a conduit to deliver primary and/or supplemental embolic materials into the outpouching. The embolic materials may include coils, liquid embolic, hydrogel, combination devices, and other embolic materials known in the art. These may most often be deployed serially to fill the contours of an outpouching. One nonlimiting example of an outpouching is a vascular aneurysm.

The present disclosure provides a mesh occluder for an outpouching or aneurysm in a vessel or an intestine which may be at least partially self-expandable and capable of immediate stabilization within moments of deployment. In some iterations, the rate of deployment of the retention arms from a compressed state within the microcatheter to an expanded state within the outpouching is controlled to be slower than the rate of expansion of the occluding or mesh element. This may allow more precise positioning of the occluding element or disc across the outpouching's neck, while avoiding the potential trauma of the retention arms being dragged across the internal walls of the outpouching. In illustrative embodiments, the present disclosure includes a self-expandable outpouching filling device having a compressed undeployed configuration and an expanded three-dimensional deployed configuration, a delivery member (such as a wire or hypotube/microcatheter), and a severable deployment system including a junction capable of releasing the self-expandable outpouching filling device. The outpouching filling element of the present disclosure, in the preferred embodiment, is constructed of a metal such as platinum or platinum alloys, nitinol, and/or other biocompatible metals. The severable deployment element may be mechanically, electrolytically, or thermally, hydrostatically, chemically, or otherwise severed to separate the self-expandable outpouching filling device from the delivery member.

These and other aspects and advantages of the disclosure will become apparent from the following detailed description and the accompanying drawings, which illustrate by way of example the features of the disclosure.

DETAILED DESCRIPTION

In illustrative embodiments, the present disclosure may be utilized to retain one or more embolic coils introduced within an outpouching, e.g., an aneurysm in a vessel or in a gastro-intestinal organ, to assist in retaining the embolic coils within the outpouching and also provide immediate support within the outpouching potentially minimizing the potential for rupturing of the outpouching or aneurysm. More specifically, the present disclosure provides an occluding device and one or more retention arms which may inter-engage with one or more embolic coils thereby preventing release of the coils though the neck of an outpouching or aneurysm, particularly, large necked aneurysms. It is further envisioned that the mesh occluder may engage any embolic agents such as hydrogel introduced within the outpouching further minimizing the potential of embolic coil migration.

In other illustrative embodiments, the present disclosure may be utilized independent of the introduction of embolic coils and/or any other embolic matter or elements. In this illustrative embodiment, the occluding component or mesh may define a more fine or dense mesh material to function as an occluder and, in conjunction with the retention arms, secure the occluder element relative to, and across, the neck as a stand-alone unit. Regardless, it is envisioned that the present disclosure will minimize, if not totally eliminate, the necessity of multiple embolic coils, which provides substantial advantages in minimizing aneurysm rupture or other difficulties.

The present disclosure provides a structure which is immediately stabilized relative to the wall of the outpouching or aneurysm. This immediate stabilization minimizes the potential of displacement of the device, thereby removing potential necessity of closing, repositioning and redeployment of the device minimizing damage to vessels and decreasing operative time. The present disclosure employs an occluding component in the form of a mesh element as well as components that secure its position relative to an outpouching before detachment, and before placement of additional embolic materials when needed. Thus, the present disclosure, in illustrative embodiments, provides a self-expandable outpouching filling device that can both cover the neck of an outpouching or aneurysm and serve as a permanent embolic plug in the outpouching, with elements that promptly stabilize its position, with the mesh component in its desired position across the neck of the outpouching, but not projecting into the parent vessel.

Figure 1:
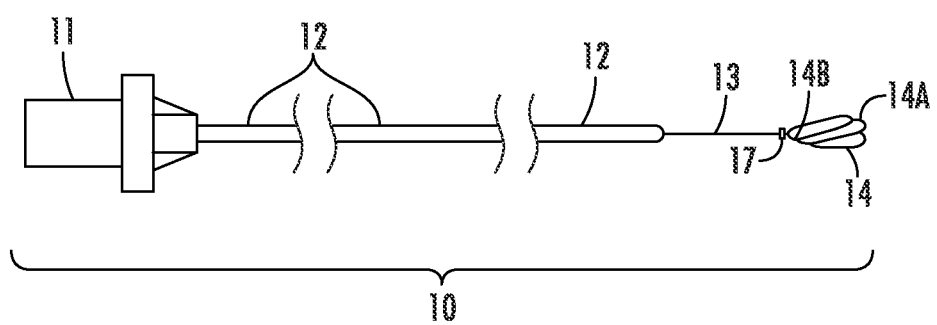
FIG. 1 illustrates the medical system including a handle or control element, a microcatheter extending from the handle, a delivery component at least partially disposed within the microcatheter and an occluding component of the mesh occluder at the distal end of the delivery component in accordance with the principles of the present disclosure.

Referring now to FIG. 1, there is illustrated the medical system in accordance with the principles of the present disclosure. The medical system 1 includes a handle or control element 11 having a housing or frame dimensioned for manipulation by the user, a catheter or microcatheter 12 extending from the handle 12 and a delivery member 13 at least partially extending through the microcatheter 12 and optionally attached to the control element 11. Attached to the delivery member 13 is a mesh occluder 14. The mesh occluder 14 is deployable for ameliorating the outpouching and will be discussed in greater detail hereinbelow. The mesh occluder 14 is an occluding component and may or may not be a mesh device. However, for simplicity, the mesh occluder 14 will be referred to hereinafter as a "mesh occluder" for simplicity. However, it is appreciated the occluder may be solid, perforated, contains slits etc.

The microcatheter 12 may be manipulated via the control element 11, and may include wires, for example, embedded within the wall of the microcatheter 12 which may be manipulated to navigate the microcatheter through a tortuous vessel, (e.g., a vascular vessel or an intestinal organ). The control element 11 may include one or more controls which assist in navigating the microcatheter 12 through the vessel. For example, the control element 11 may include circuitry, electronics, etc. capable of sending signals to the microcatheter 12 to manipulate the wires within the microcatheter 12 to laterally move sections of the microcatheter 12 and/or send signals to the delivery member 13. The delivery member 13 may be a solid wire, or in the alternative, a hypotube. The delivery member 13 may have a detachment element 17 at its distal end utilized to detachably secure the mesh occluder 14 to the delivery member 13. In illustrative embodiments, the control element 11 may send electrical signals, energy, etc. to the detachment element 17 to effect detachment of the mesh occluder 14. In one illustrative embodiment, the control element 11 may be a stand-alone unit (e.g., commercially available) and coupled to the microcatheter 12 and/or the delivery member 13 prior to performance of the surgical procedure. In other embodiments, the control element 11 is a permanent component of the medical system 1. It is envisioned that the medical system 1 may be entirely disposable after a single use or reusable in part or in whole. If reusable, the component of the medical system may be fabricated from materials capable of withstanding conventional sterilization procedures. The microcatheter 12 may include one or more exterior mounted balloons to facilitate retention of the microcatheter relative to the vessel and the outpouching. The microcatheter 12 may have an outer diameter of 0.5 Fr.-20 Fr. In one embodiment, the microcatheter 12 has an outer diameter ranging from 3 Fr. to 5 Fr.

Figure 2:
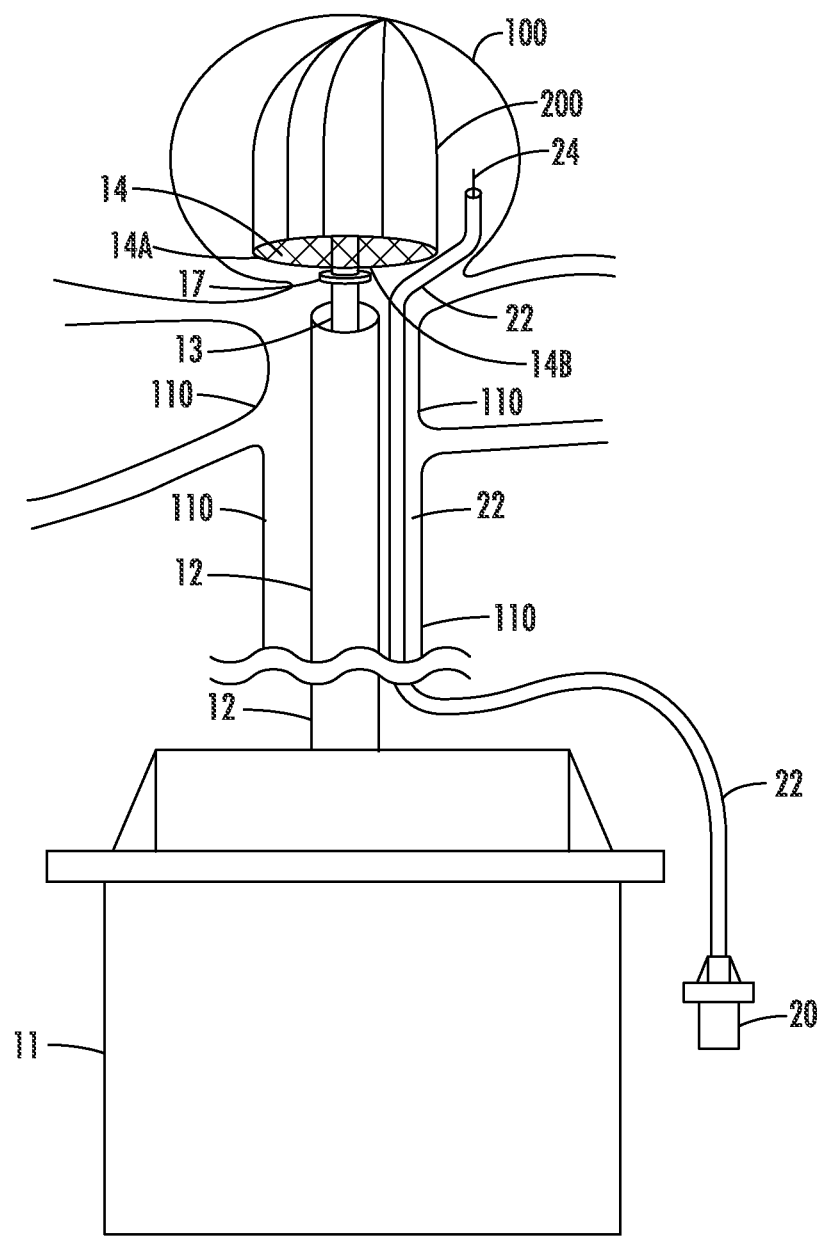
FIG. 2 is a side elevation view illustrating the microcatheter of the medical system accessing, through a vessel, an outpouching, and with the mesh occluder deployed relative to the outpouching with the occluding element at least partially spanning the neck of the outpouching and the retention arms in the form of one or more coils deployed within the interior of the outpouching in accordance with the principles of the present disclosure.

Referring now to FIG. 2, there is illustrated the microcatheter 12 introduced within a vessel 110 and the mesh occluder 14 deployed relative to the target outpouching (e.g., an aneurysm) 100. A contrast agent may be utilized to assist in locating the microcatheter 12 and the mesh occluder 14 relative to the outpouching as is known in the art. The deployment of the mesh occluder 14 may be effected through a number of mechanisms. In one illustrative embodiment, the mesh occluder 14 including the mesh occluding component and the retention arms 200 may be disposed within the microcatheter 12 in a compressed state. The control unit 11 may be manipulated to advance the delivery member 13 to eject the mesh occluder 14 out the distal end of the microcatheter 12. Once exposed from the microcatheter 12, the mesh occluder 14 assumes a normal expanded state. In the normal expanded state, the mesh device of the mesh occluder 14 at least partially extends across the neck of the outpouching 100 and the retention arms 200 deploy within the interior of the outpouching, for example, engaging the interior walls of the outpouching to facilitate retention of the mesh occluder 14 relative to the neck of the outpouching.

In illustrative embodiments, the mesh occluder 14 is a mesh disc, and, may optionally be coated with a hydrogel. In the following discussion, the terms "mesh occluder" and "mesh disc" are interchangeable. For the treatment of saccular outpouchings (or aneurysms), an endovascularly deployed mesh (metal mesh or other mesh) disc 14 may optionally have two layers similar to the Anplatz Left Atrial Appendage closure device currently in trials. The mesh disc 14 can have versions that are relatively flat, or some versions where the edges are folded up to accommodate differently shaped outpouchings (or aneurysms), including very wide neck outpouchings (or aneurysms). Such deviations from the generally flat plane of the mesh occluder or disc 14 of the present disclosure may have turned-up sides which conform to the walls of a target outpouching 100 which are proximal to the neck of the outpouching 100. Such upturned elements 14A (sometimes referred to as "lips") (FIG. 3A) are optional and optimally used for very wide neck outpouchings (or aneurysms) that are less spherical in shape and more cylindrical in shape. With more wide-neck outpouchings (or aneurysms) the anatomy does not lend itself to the deployment of a flat mesh disc 14 because wide neck outpouchings (or aneurysms) lack sufficient overhang regions at the neck to support the mesh disc 14. Thus, in accordance with the present disclosure, lips 14A are provided on the mesh disc 14 along with one or more retention arms 200 to facilitate the attachment to the wide neck aneurysm. The retention arm or extensions 200 provide supplemental support to be secured with an outpouching. The securement, unlike the prior art, provides a mesh disc with multiple attachment points within an outpouching. More particularly, the mesh disc 14 comprises a core 14B having a diameter configured to be smaller than the target outpouching 100. The core 14B of the mesh disc 14A is secured in place by at least one attached extension or retention arm 200. In the alternative, the occluding component may be a slightly arcuate mesh element.

In illustrative embodiments, the retention arms 200 form a looped coil matrix with at least portions of the arms 200 engaging the internal wall of the outpouching. In one illustrative embodiment, the retention arms 200 form a dome shape with at least some of the arms connected at one or more locations. In other embodiments, the retention arms are independent, and can assume any configuration including the dome-shaped matrix shown in FIG. 2.

The advantage of the looped coil matrix is that they will provide a structure by which the mesh disc 14 can achieve more immediate and effective stable positioning, by the coil loops gripping the wall of the outpouching, with the mesh portion optimally positioned at the neck of the outpouching. The coil loops may be spiral or connected in the form of a birdcage (or dome-shape) or similar structure. The prior art, however, teaches essentially spherical or ovoid configurations, and lacks the more effective dome-like shape and dense, somewhat flattened mesh at the bottom (neck of the outpouching) proximal to the distal end of the catheter.

As mentioned hereinabove, the occluding device 14 and the retentions arms 200 may be formed of a shape memory material, and may, optionally or alternatively, assume the expanded shape in response to thermal energy, for example, upon exposure to the thermal surroundings of blood, etc. In the alternative, the surgical device may be formed of a spring steel or metal. The occluding component 14 and the at least one retention member or arm 200 are compressible into a shape suitable for delivery through the microcatheter 12. As also noted, the properties of the occluding device 14 and the retention members 200 may be controlled whereby the occluding device expands at a faster rate than the retention arms 200 to minimize potential of undesired "dragging" of the retention arms 200 within the walls of the outpouching. Other arrangements are also envisioned.

In other illustrative embodiments, the control unit 11 which is in electrically coupled relation with to the detachment member 17 may relay signals to the occluding component 14 to initiate decompression of the occluding component 14 and at least one retention arm 200 prior to deployment, or cause expansion of the occluding component 14 and the retention arms to its expanded state subsequent to deployment from the microcatheter 12. For example, control element 11 may incorporate mechanical, chemical, hydrostatic, electrical and/or thermal means for implementing the function of deploying the occluding component 14 and the retention arms 200, and detaching the surgical device 14 from the detachment element 17. For example, electrical signals and/or thermal energy can be delivered from control unit 11 conveyed through the delivery member 14 to cause, in response to generated thermal energy, the surgical device 14 to assume its expanded state via shape memory characteristics, and optionally break a detachable attachment of the detachment element 17 and the surgical device 14. Subsequent to deployment, the control unit 11 may be effected to cause retraction of the microcatheter 12 and/or the delivery member 13 relative to the outpouching.

Referring still to FIG. 2, the mesh disc 14 and at least one retention arm 200 are deployed through delivery catheter 12 passing through vessel 110 to the base of the neck of target saccular outpouching 100. Control device 11 may optionally signal delivery member 13 to extend beyond the distal end of catheter 12 in a length sufficient to enter target outpouching 100 to allow deployment of mesh disc 14 and at least one retention arm 200. Once the progress of delivery member ceases, control element 11 signals mesh disc 14 and at least one retention arm 200 to deploy. Mesh disc 14 and at least one retention arm 200 enter the target outpouching in a compacted form, the signal from control element 11 directs the mesh disc 14 and at least one retention arm 200 to open as a blossom to allow the perimeter of the mesh disc 14 and at least one retention arm 200 to overlap the base of the neck of the outpouching 100. In one illustrative embodiment, the control unit 11 and the microcatheter 12 are manually held in place while the delivery member 13 is manually advanced forward in a length sufficient to enter the target outpouching 100 to allow deployment of the mesh disc 14 and at least one retention arm 200. The mesh disc 14 and at least one retention arm 200 enter the target outpouching in a compacted form and as it is released from its constraint, the mesh disc 14 and at least one retention arm 200 open to allow the perimeter of the disc mesh disc 14 and at least one retention arm 200 to overlap the base of the neck of the outpouching 100. The disc is then gently pulled back manually into position, which is determined preferentially by fluoroscopic and/or angiographic images.

Figure 3A:
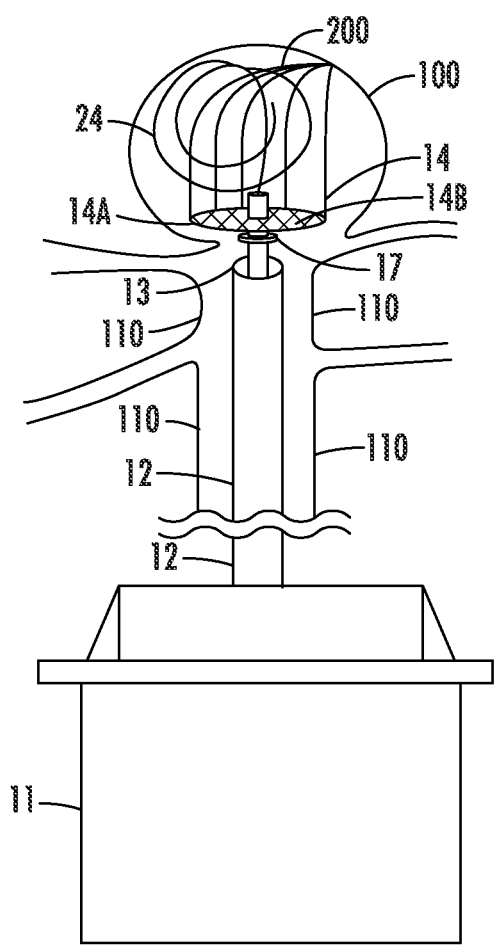
FIG. 3A is a side elevation view similar to the views of FIGS. 2-3 illustrating the occluding component deployed at base of neck of a targeted, non-spherical outpouching.
Figure 3B:
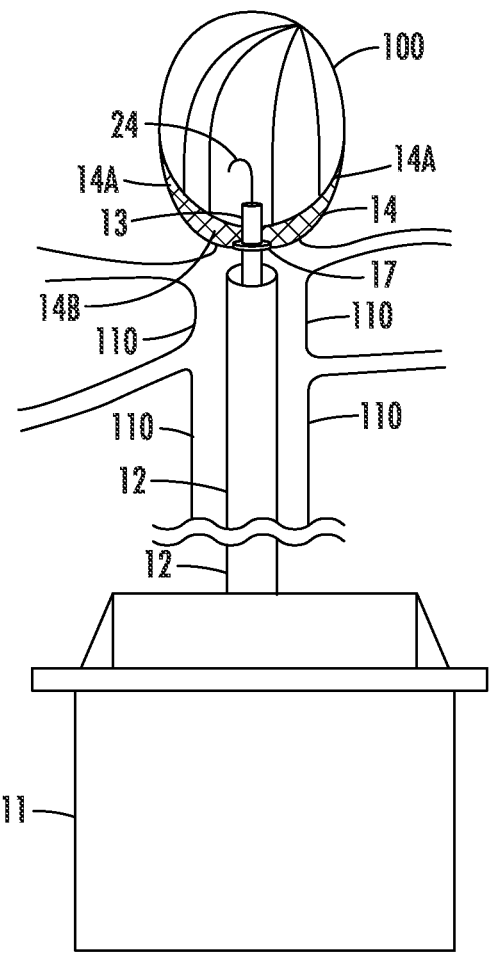
FIG. 3 is a side elevation view similar to the view of FIG. 2 illustrating a control element of the medical system delivering an embolic coil within the outpouching in accordance with the principles of the present disclosure.

For the treatment of saccular outpouchings (or aneurysms), an endovascularly deployed mesh (metal mesh or other mesh) disc may be utilized and incorporate at least two layers, The disc can have versions that are relatively flat, or some versions where the edges are folded up to accommodate differently shaped outpouchings (or aneurysms), including very wide neck outpouchings (or aneurysms). Such deviations from the generally flat plane of the occluding device, in the form of the mesh disc 14 may have turned-up sides which conform to the walls of a target outpouching 100 which are proximal to the neck of the outpouching 100. As best depicted in FIG. 3, and, in particular FIG. 3A, the upturned elements 14A (sometimes referred to as "lips") are optional and optimally used for very wide neck outpouchings (or aneurysms) that are less spherical in shape and more cylindrical in shape. With the more wide-neck outpouchings (or aneurysms) lips 14A provide sufficient overhang at the neck to support the mesh disc 14 adjacent wide neck outpouchings (or aneurysms). The present disclosure contemplates the use of multiple distinct lip configurations. The lip configurations differ in diameter, shape and orientation. In the preferred embodiment the central portion of the mesh disc (i.e. the portion closest to the delivery member, such as the wire or deliver microcatheter) will be oriented parallel to the neck of the target outpouching.

The diameter of the mesh disc ranges from 0.1 mm to 30 cm. The shape of the mesh disc ranges from a circle to triangle. The shape is most typically round or oval. The mesh disc 14 may be coated with hydrogel. The interstices of the disc 14 may be dimensioned to contain the hydrogel.

In a typical spherical outpouching with a narrow neck, the entire mesh disc 14 and at least one coil-arm 200 include the lips 14A and should be oriented parallel to the neck of the target outpouching. In this case, the lips overhang and rest on the base of the target outpouching, completely covering the neck of the target outpouching and extending over a portion of the adjacent base of the target outpouching and forming a base for at least one retention arm 200.

In a typical non-spherical outpouching with a wide neck, the entire outer perimeter of the mesh disc 14 should be oriented more perpendicular to the neck of the target outpouching than in the case of the typical spherical outpouching with a narrow neck, so as to gently grip the walls near the base of the target outpouching.

Referring again to FIG. 2, the medical system 1 may further include, or be utilized with, a coil delivery mechanism including a second control unit 20 and a second catheter 22 for delivering one or more embolic coils 24 into the outpouching either prior to, subsequent to or in conjunction with the deployment of mesh occluder 14. The embolic coils 24 may be any conventional embolic coil utilized to treat an aneurysm or any outpouching within a vessel of a body. It is envisioned that the mesh occluder 14 including the occluding or mesh component 14 and the retention arms 20 will further assist in retaining the embolic coils 24 within the outpouching. For example, the occluding component 14 may prevent release of the micro coils 24 through, for example, interfering with the movement of the embolic coils e.g., micro coils, 24 within the outpouching or engaging the micro coils 24, for example, at least partially engulfing or wrapping around the micro coils 24. It should be noted that mesh disc or occluding element 14 of the present disclosure is capable of resulting in a second "j ailed" microcatheter. FIG. 3 depicts the introduction of one coil 24 within the outpouching. As noted, a plurality of embolic coils 24 may be introduced within the outpouching during or even subsequent to the initial procedure.

As discussed hereinabove, following deployment of the occluding component 14 and at least one retention arm 200, the control element 11 is optionally capable of sending signals which result in the deployment of coils 24, hydrogel 16, and/or lips 14A. As noted, in one illustrative embodiment, the separate control element 20 controls detachment of coils 24. Following deployment of the aforementioned elements, the control element 11 is capable of signaling detachment element 17 to separate delivery member 13 from the mesh disc 14 and at least one retention arm 200. Control element 11 is then capable of retracting catheter 12 and delivery member 13.

The present disclosure can be used with or without hydrogel 16. One illustrative embodiment is devoid of hydrogel. However, it should be noted that the current disclosure can be used with hydrogel, and such use has been disclosed in prior applications submitted by the Applicant. When hydrogel is employed, hydrogel can optionally expand to a specific external stimulus only, rather than time of hydration. Hydrogel may potentially shrink to an optional external stimulus. This on-demand expansion and shrinkage is helpful for repositioning medical tools near target areas inside veins and arteries. The external stimuli include, but are not limited to, thermal, electrical, and/or chemical signals. It should also be noted that hydrogel 16 can optionally be radio-opaque, which facilitates remote locating and positioning of the hydrogel 16, this embodiment has been disclosed in prior applications, such as in Application Serial No. in application Ser. No. 16/024,673 to Walzman.

Note that the mesh disc 14 and at least one retention arm 200 will be held in position upon deployment by coils 24 or hydrogel 16, each of which will substantially conform to the interior of target outpouching 100. The retention arm 200 may be a loop, or a straight extension. The extensions may be of various widths and shapes. Some embodiments may have rounded atraumatic edges. Alternatively, the mesh disc 14 has up going "lips" 14A and can be held in place by friction between the disc and the walls of the target outpouching, as well as the fact that the disc 14 has a greater diameter than the diameter of the neck of the outpouching 100. Lastly, a larger disc 14 can be held in place both ways.

The amount of hydrogel 16 may vary. The specific amount is not significant as long as sufficient hydrogel 16 is deliverable to the outpouching 100 to fill it. Other embodiments may use no hydrogel. In an alternate embodiment of the present disclosure, optional hydrogel coats mesh disc 14 and at least one retention arm 200 such that the hydrogel will expand into and filling the dome of the outpouching 100.

Mesh disc 14 and at least one arm extension 200 are, in the preferred embodiment, radio-opaque or have radio-opaque marker or other positioning markers or incorporates other technology for remote visualization and location detection. The same characteristic is incorporated in detachment element 17.

Referring now to FIG. 3, the present disclosure may incorporate elements of the prior art, such as the deployment of coils 24 through microcatheter 13.

Referring now to FIG. 3A, the present disclosure teaches the use of up turned lips 14A to secure the mesh disc 100, integrating wire embolic coil 24 of the prior art. FIG. 3A also depicts an embodiment in which the delivery member 13 is a microcatheter capable of acting as a conduit for delivery of coils through it.

Figure 4:
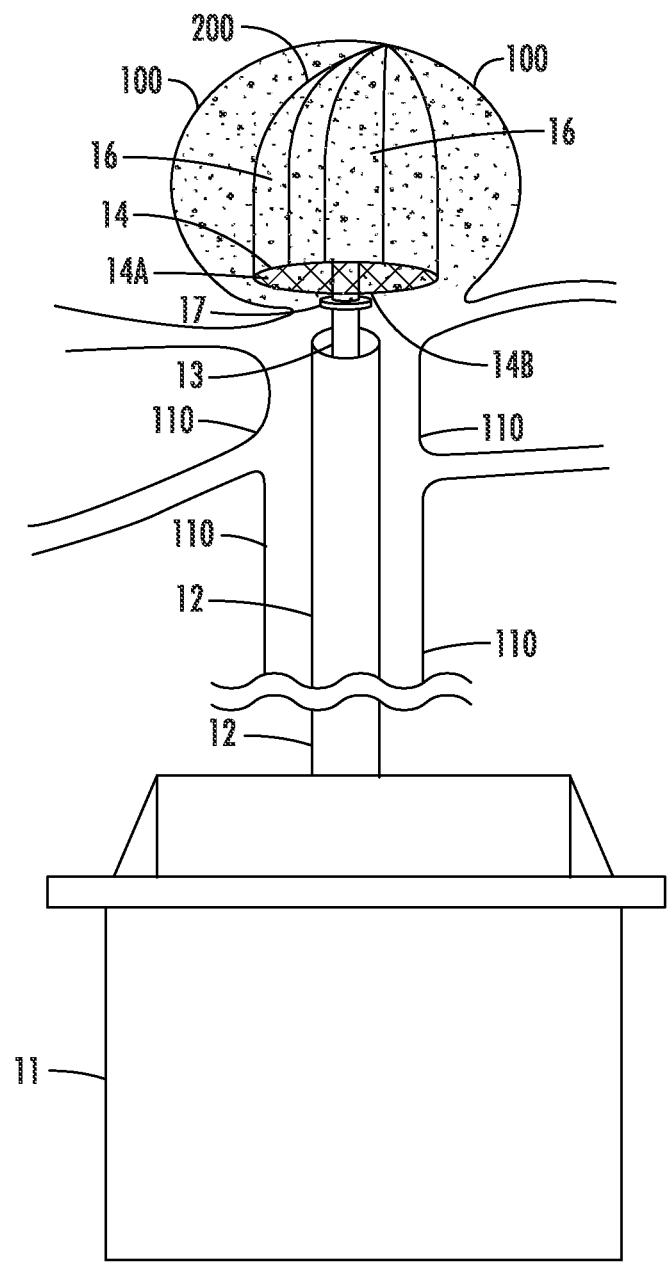
FIG. 4 is a side elevation view similar to the views of FIGS. 2-3 illustrating introduction of an embolic agent, for example, a hydrogel, within the outpouching in conjunction with deployment of the retention arms.

Referring now to FIG. 4, an alternate embodiment of the present disclosure deploys mesh disc 14 and at least one retention arm 200 in conjunction with semitransparent, activated/swollen hydrogel 16. Hydrogel 16 can be deployed on the surface of mesh disc 14 and at least one retention arm 200, via a hollow in delivery member 13, via a second device (not shown), or via a second wire (not shown) deployed through catheter element 12. Alternatively, the hydrogel 16 may be deployed via the mesh disc 14 and at least one retention arm 200. Alternatively, hydrogel embedded coils may be used with the present disclosure.

Figure 5:
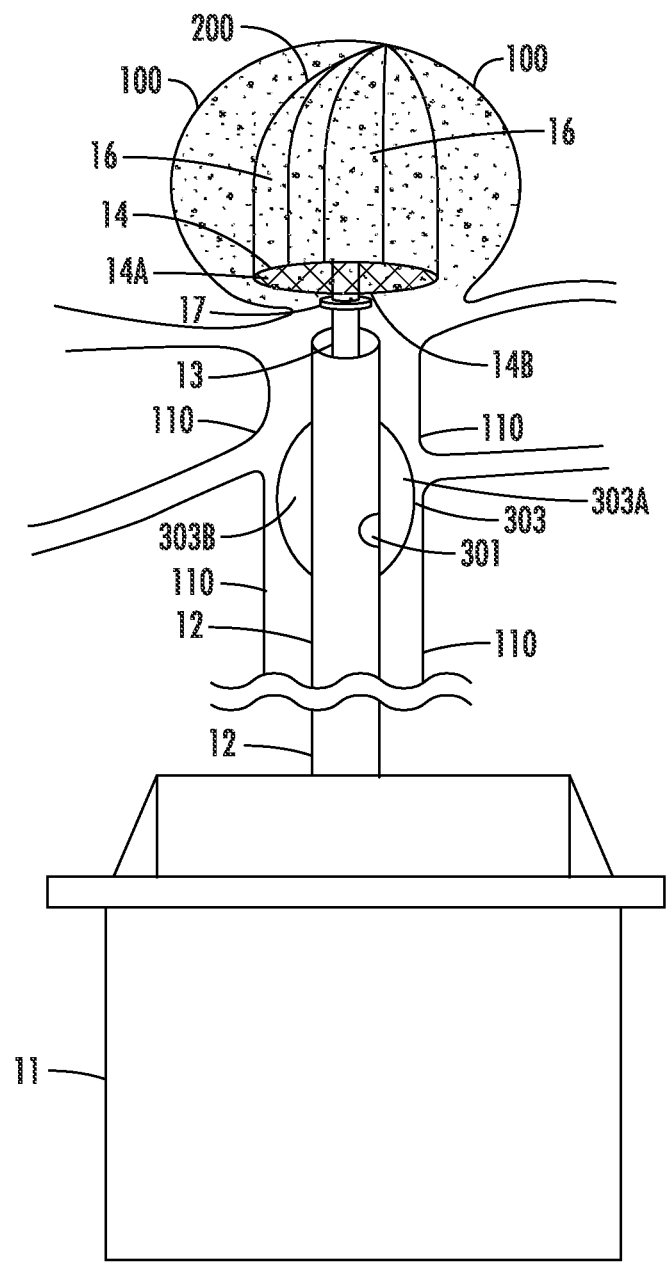
FIG. 5 is a side elevation view similar to the views of FIGS. 2-4 illustrating an optional positioning balloon coupled to the outer surface of the microcatheter to position the microcatheter relative to the outpouching.

Referring now to FIG. 5, an alternate embodiment of FIG. 4 further includes a centering balloon 303 within vessel 110. The centering balloon 303 allows catheter element 12 to be positioned more precisely and stably in relation to the center of the neck of target outpouching 100. Prior to deployment, additional contrast or other fluid injections can optionally be used to initiate deployment of optional balloon(s) 303 or 300 for the purpose of positioning catheter 12 so as to center delivery microcatheter 13 for optimal deployment of mesh disc 14. Referring more particularly to the centering balloon 303, the balloon is described in detail in Walzman application Ser. No. 14/482,436 (entitled Vessel access catheter), incorporated herewith by reference.

It should be noted that Walzman application Ser. No. 14/482,436 (entitled "Vessel Access Catheter"), incorporated herewith by reference, describes both single balloons and balloon arrays. The centering balloon 303 may be either a single balloon or a balloon array. The single balloon or balloon arrays are designed to assist in centering the tip of catheter element 12 to a location proximal to the center of the target outpouching. The positioning may be achieved by the inflation of at least one balloon in order to deflect catheter element 12 in a desired direction.

Figure 6:
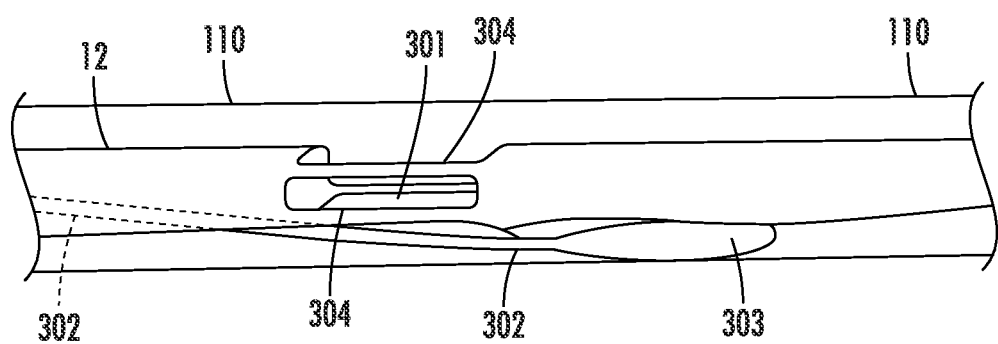
FIG. 6 is a side plan view illustrating illustrates a detailed deployment of an optional disc balloon.

An additional embodiment of the current disclosure incorporates the Walzman disc balloon 300, as illustrated by FIG. 6, into catheter element 12. The incorporation is an alternate embodiment which is designed to help center the tip of catheter element 12 to a location proximal to the center of the target outpouching. It may also act as vertical positioning element by abutting the base of the mesh disc during positioning in the target outpouching.

Both balloon embodiments separately or in combination are also designed to arrest flow within the vessel proximate to the target outpouching when fully inflated. The inflation will result in control of unwanted bleeding in case of target outpouching rupture.

Thus, the present disclosure can have several different embodiments, including:

First, a disc alone—an appropriately sized disc—can be deployed through a microcatheter in a saccular aneurysm, after a second microcatheter is placed in the microcatheter.

The disc is gently pulled back to the neck of the outpouching, bridging the neck, and with a lip beyond the open portion of the neck to stabilize the disc. The disc is not detached at first, but remains tethered to its delivery element 13 (a wire or catheter). Were it to be deployed early it would likely migrate into the outpouching and be ineffective. Through the second microcatheter, which is now "jailed" in the outpouching, appropriately sized embolic coils are sequentially placed and deployed into the outpouching per current routine protocols/techniques, until the outpouching is adequately filled with embolic coils. The second microcatheter is removed. At this point the disc is detached from its delivery wire/catheter, which is removed.

Second, a disc mounted on a hypotube or delivery member 13 is introduced into the outpouching through a slightly larger catheter, wherein the hypotube or delivery member 13 goes through the disc to extend just beyond it. An appropriately sized disc can be deployed through a microcatheter in a saccular aneurysm. The disc 14 is gently pulled back to the neck of the outpouching, bridging the neck, and with a lip 14A beyond the open portion of the neck to stabilize the disc 14. The disc 14 is not detached at first but remains tethered to its delivery member/hypotube 13. Were it to be detached early, it would likely migrate into the outpouching and be ineffective. Through the delivery catheter/microcatheter, appropriately sized coils are sequentially placed and deployed into the outpouching per current routine protocols/techniques, until the outpouching is adequately filled with coils. At this point the disc 14 is detached from its delivery member/hypotube. The delivery member/hypotube 13 is then removed.

Third, a hydrogel enhanced disc 14 alone is provided. The disc 14 is an endovascularly deployed mesh composed of a shape-memory material such as nickel-titanium alloy or other memory-shape material capable of super-elastic properties, such that the compressed mesh disc 14 will revert to its flat-mesh disc shape upon release or activation by an electronic or light impulse. It will optionally have two layers similar to the Anplatz Left Atrial Appendage closure device currently in trials—the disc can have versions that are relatively flat, or some versions where the edges are folded up to accommodate different shape outpouchings (or aneurysms), including very wide neck outpouching. In this version, however, the outside surface of the disc facing into the outpouching is lined with a non-biodegradable hydrogel, that when exposed to blood upon deployment, will swell over a prescribed time (10 minutes in the preferred embodiment of the present disclosure), to conform to the size and shape of the outpouching, and fill and occlude the outpouching. The other layer of the disc 14 that is closer to the parent artery can optionally have thin layers of hydrogel as well—but this layer would have hydrogel designed only to swell to occlude that layer of disc alone, so no hydrogel from the other layer can potentially expand through the mesh into the parent vessel. An appropriately sized disc 14 can be deployed through a microcatheter in a saccular aneurysm. The disc is gently pulled back to the neck of the aneurysm, bridging the neck, and with a lip beyond the open portion of the neck to stabilize the disc. The disc is not detached at first but remains tethered to its delivery system (a wire or catheter). Were it to be detached early it would likely migrate into the outpouching and be ineffective. The disc is held in place at the neck of the outpouching, while the hydrogels swell. Once the prescribed time is elapsed and follow up angiography confirms occlusion of the outpouching, the disc is detached from its delivery wire/catheter, and the delivery wire/catheter and the microcatheter through which it was deployed are removed. Optionally in appropriate circumstances, hydrogel may be used in filling the outpouching, which occludes that outpouching and also stabilizes the disc in place (in example 1 and 2 above the coils achieve these 2 goals).

Fourth, all features of the first through third above may be included, and optionally, the disc can have a smaller metal core disc 14B (FIG. 2) dimensioned smaller than the diameter of the outpouching and having hydrogel designed to expand out in a disc like shape from the edges, to make a larger disc that can then be gently dragged into position. It can then be pinned in place by coils or optional hydrogel embedded in the top of the disc, that also then expands into the dome of the outpouching, either via a layer on the top of the metal disc designed to expand after the side hydrogel, or via a separately implanted hydrogel bead or the like.

A smaller disc can also be used in combination with other embolic fillers, wherein the disc is secured by the at least one arm extension, and the disc serves to reduce the effective width of the neck of the outpouching.

The mesh disc 14 and at least one retention arm 200 may also optionally be delivered through a disc balloon microcatheter (previously described by Walzman Ser. No. 14/732, 170) or a similar configuration (disc balloon), an intermediate catheter, or another balloon catheter. These can serve as methods for delivering the occluding component of the present disclosure. The method(s) may also be used to deliver any mesh intrasaccular device including other devices taught by the prior art, such as the Web and the Luna.

The advantage of a delivery through a disc balloon microcatheter is twofold. First, the balloon may sometimes be helpful in positioning the mesh disc 14 and at least one retention coil-arm 200, and second, that in the event the outpouching ruptures during treatment, the balloon can be inflated to arrest flow and control active bleeding until more coils can be placed.

The disc and the retentions arms 200 as coil loops vary in size and in the time necessary to fully deploy. More particularly, the diameter of the discs varies from 0.1 mm-500 mm. The diameter of the coil loops varies from 0.1 mm-1000 mm. The length of the coil loops can be 0.1 mm-3142 mm long. Coil loops for coil disclosure are typically sized in diameter of the target outpouching.

With respect to the time necessary to fully deploy the disc and the coil vary from nearly instantaneously [approximately one second or less] to one hour. While in some embodiments, both the disc 14 and the retention arm 200 or coil expand at the same rate, in other embodiments the disc and the coil expand at independent rates. In some embodiments the coil expands faster than the disc and in other embodiments the disc expands faster than the coil.

In the preferred embodiment the retention arms 200 or coils complete their expansion approximately forty-five (45) seconds after the disc completes its expansion. This time off set allows the occluding component to be positioned into optimal position across neck (the opening) of the target outpouching without dragging metal under outward tension along the target outpouching or vessel walls thus eliminating or ameliorating medical difficulties such as breaching the outpouching or the vessel walls. The breaches can result in injury or death to a patient.

The present disclosure has at least four structural optional elements. The optional element are central donut holes in the disc element of the present disclosure; single or multiple mesh layer(s) in the disc element of the present disclosure; hydrogel coating on all or parts of the disc element of the present disclosure; and hydrogel coating of all or parts of the retention arm element(s) of the present disclosure.

More particularly, the donut hole structure in the disc element of the present disclosure is optional. One embodiment of the present disclosure has a central donut hole structure. Another embodiment of the present disclosure does not have a central donut hole structure.

More specially, the single layered mesh configuration of the present configuration is optional. One embodiment of the present disclosure has a single mesh layer in the disc element of the present disclosure. Another embodiment of the present disclosure the present disclosure has multiple mesh layers in the disc element of the present disclosure.

The application of a hydrogel coating of the disc element of the present disclosure is optional. One embodiment of the present disclosure discloses a hydrogel coating on the surfaces of the disc element 14 of the present disclosure. In another embodiment of the present disclosure, the hydrogel coating is not applied to the surfaces of the disc element 14. In other embodiments, a hydrogel coating is employed on some but not all surfaces of the mesh disc 14. In some optional embodiments, the hydrogel is chemically optimized to expand significantly, and may also be positioned so that it expands, into the pathological outpouching, to further aid in the thrombosis/closure of the aneurysm/outpouching.

Furthermore, the application of a hydrogel coating of the retention arm element(s) 200 of the present disclosure is optional. One embodiment of the present disclosure discloses a hydrogel coating on the surfaces of the retention arm element(s) 200. In another embodiment, the hydrogel coating is not applied to some of the surfaces of the retention arm element(s) 200. In yet another embodiment of the present disclosure, the hydrogel coating is not applied to any of the surfaces of the retention arm element(s) 200.

Figure 7:
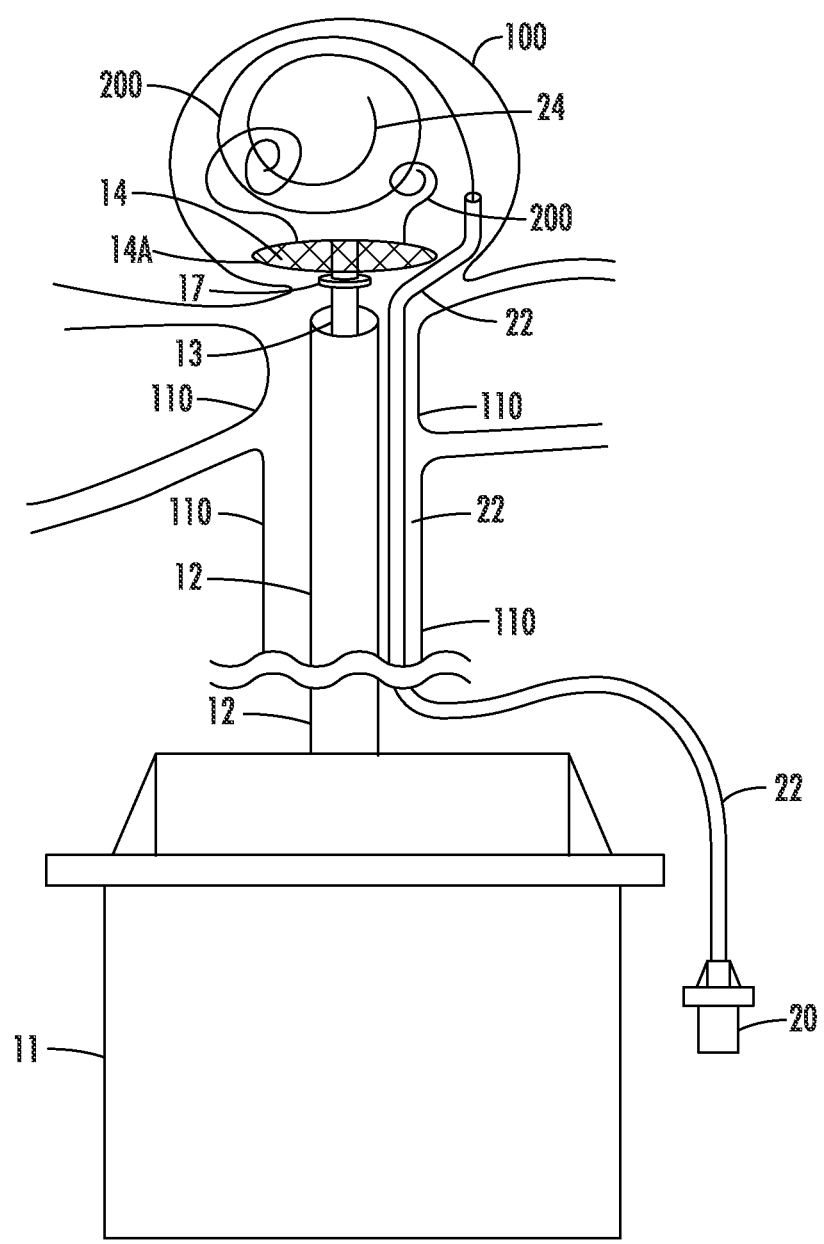
FIG. 7 is a side elevation view illustrating deployment of multiple independent retention members within the outpouching.

Referring now to FIG. 7, there is illustrated another embodiment of the present disclosure. At least one or more retention arms 200 in the shape of a coil are attached to the mesh component and extend within the outpouching. The retention arms 200 may engage the internal wall of the outpouching and/or the embolic coil 24 to assist in retention of the embolic coil 24 and the mesh disc or occluder 14 relative to the neck of the outpouching wall.

Figure 8:
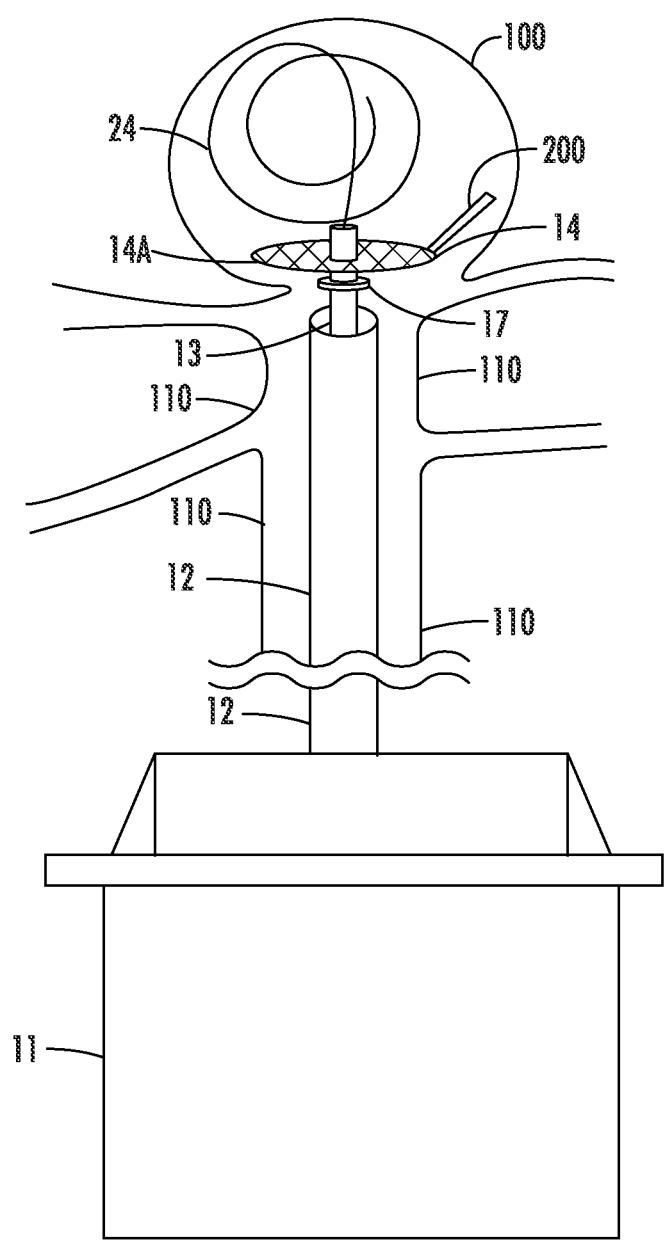
FIG. 8 is a side elevation view illustrating deployment of a single retention arm having a generally linear configuration within an outpouching.

FIG. 8 illustrates an embodiment utilizing a substantially linear retention arm 200 which may be advantageous is small outpouchings or outpouchings having atypical shape. The ends of the linear retention arms 200 may be blunt to avoid any potential undesired engagement with the wall of the outpouching. Also, in accordance with this embodiment, the embolic coil 24 is delivered through the microcatheter 12.

Figure 9:
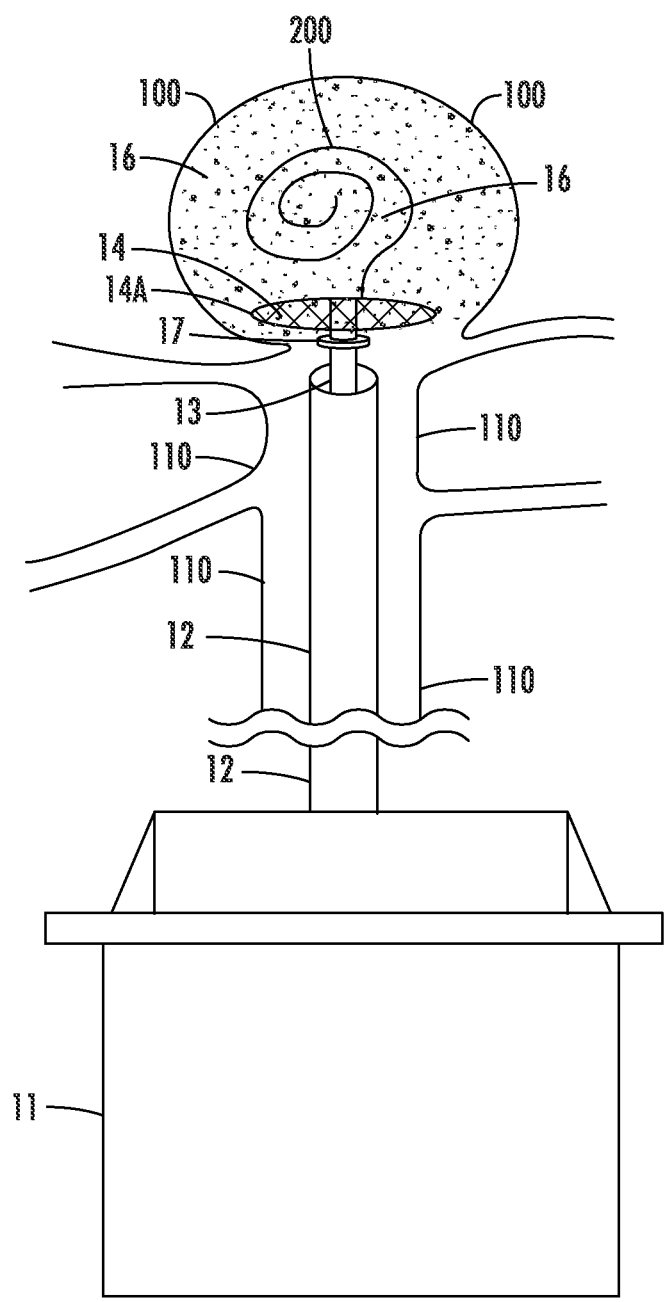
FIG. 9 is a side elevation view illustrating deployment of a single retention arm having a generally coiled configuration within an outpouching filled with hydrogel.

FIG. 9 illustrates an embodiment where a single coiled retention arm 200 coupled to the mesh disc or occluder 14 is embedded within an outpouching filled with hydrogel 16. The retention arm 200 engages the hydrogel 16 in a manner which minimizes movement of the retention arm 200 and subsequent dislodgement of the mesh occluder 14. No embolic coils are utilized in this embodiment. It is envisioned that the mesh occluder 14 may function as a stand-alone flow diverter in conjunction with the hydrogel 16.

Figure 10:
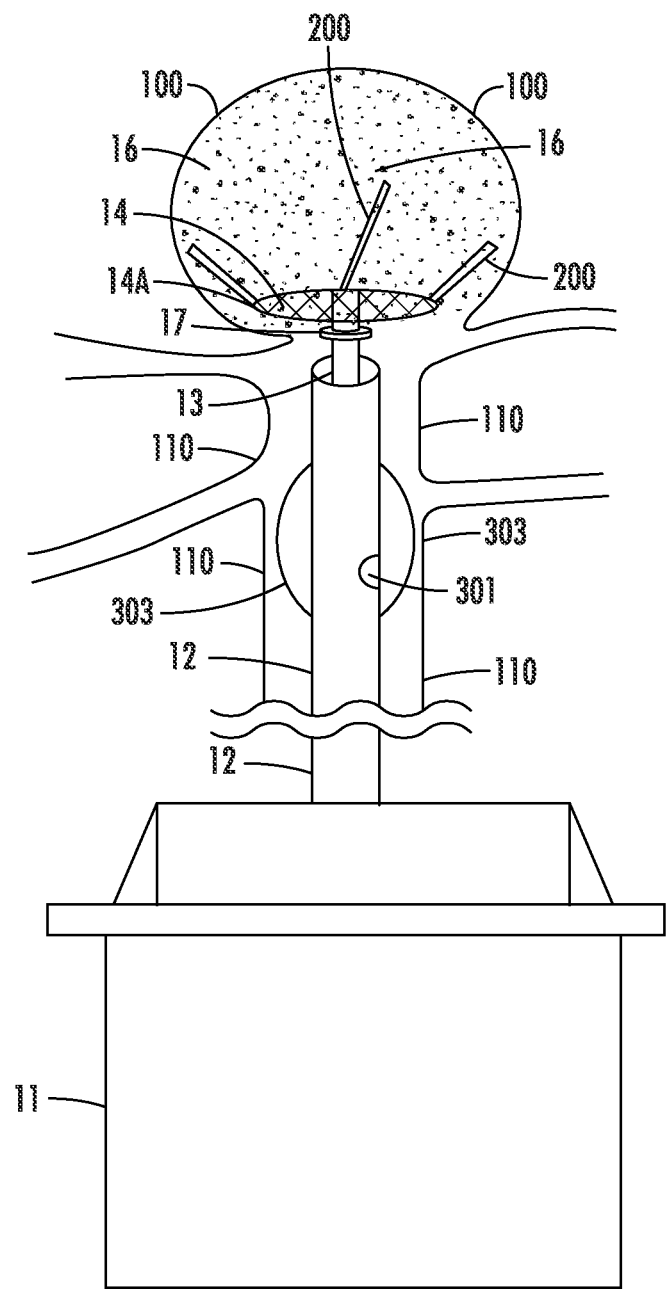
FIG. 10 is a side elevation view illustrating deployment of a multiple retention arms each having a generally linear configuration within an outpouching filled with hydrogel.

FIG. 10 is a similar embodiment to FIG. 9 but utilizes a plurality of substantially linear retention arms 200 attached to the mesh occluder 14.

Illustrative embodiments utilize multiple coiled retention arms attached to the mesh occluder 14 (e.g., as depicted in FIG. 7). In accordance with these embodiments, the retention arms 200 and the mesh occluder may function as a stand-alone flow diverter. Various configurations of the retention arms 200 are contemplated.

In other illustrative embodiments, various coiled retention arms 200 and optionally linear retention arms 200 utilized with hydrogel 16 to retain the mesh occluder 14 across the neck of the aneurysm. No embolic coils may be needed in accordance with this embodiment with the retention arms and the hydrogel functioning as a stand-alone flow diverter.

In illustrative embodiments, a mesh occluder for ameliorating an outpouching, comprises a control element, a catheter element, a delivery member, a detachment element, a mesh disc, a distal opening and at least one attached extension arm, wherein the mesh disc further comprises a proximal face and a distal face. The proximal face is opposite of the distal face. The proximal and the distal faces are substantially flat. The mesh disc 14 further comprises peripheral lips 14A. The mesh disc 14 comprises a core 14B having a diameter configured to be smaller than the outpouching, wherein the mesh disc is secured in place by the at least one attached extension arm 200.

The mesh disc with the at least one attached extension arm comprises a matrix adapted to form shapes of suitable geometry for adapting to the contours of the outpouching.

The delivery member may further comprise a channel capable of delivering at least one coil therethrough.

At least one additional coil may be serially delivered through the delivery member.

A matrix of the serially delivered coils are adapted to form shapes of suitable geometry potentially fill the outpouching.

The mesh disc 14 may be configured to be impregnated with adhered hydrogel in a sufficient amount to wedge the mesh disc into a target vascular structure.

The adhered hydrogel may be radio-opaque.

In another illustrative embodiment, an embolic device for ameliorating an outpouching, comprises a control element, a catheter element, a wire, a detachment element, a mesh disc, at least one arm extension adhered to the mesh disc, and a distal opening, wherein the mesh disc further comprises a proximal face and a distal face, the proximal face being opposite of the distal face; and the proximal face and the distal faces are substantially flat; wherein the mesh disc further comprises peripheral lips, and a disc core having a diameter configured to be smaller than the aneurysm, and wherein the mesh disc is secured in place by the at least one arm extension.

The mesh disc with the at least one arm extension comprises a matrix adapted to form shapes of suitable geometry for conforming to the contours of the outpouching.

The matrix may be configured to substantially fill the aneurysm.

The mesh disc and the at least one extension or retention arm may be configured to be impregnated with adhered hydrogel in a sufficient amount to wedge the mesh disc into a target vascular structure.

The mesh disc may be configured to be positioned at the neck of the outpouching.

The mesh disc may be configured not to substantially fill the outpouching.

The mesh disc may further comprise at least one additional layer.

The at least one additional layer may further include the adhered hydrogel adapted to alter flow through only the one additional layer.

The mesh disc with the at least one extension arm may be adapted to grip the walls of the outpouching, and configured to stabilize the mesh disc in position at the neck of the outpouching.

The device may comprise a delivery member having a channel capable of delivering at least one coil therethrough.

At least one additional coil is serially delivered through the channel of the delivery member.

At least one additional coil is serially delivered comprise a matrix adapted to form shapes of suitable geometry to fill an outpouching.

Although the disclosure has been described in detail in the foregoing embodiments for the purpose of illustration, it is to be understood that such detail is solely for that purpose, and that variations can be made therein by those skilled in the art without departing from the spirit and scope of the disclosure, except as it may be described by the following claims.

What is claimed is:

1. A medical apparatus for ameliorating an outpouching, comprising:
   an endovascular member dimensioned for insertion into the outpouching, wherein the endovascular member includes:
      a mesh, the endovascular member defining a flat distalmost surface coplanar with the mesh, whereby the endovascular member is configured as a flat disc defining a rim; and
   at least one retention arm connected to the endovascular member and extending distally and radially outward from the rim, the at least one retention arm configured to engage a wall of the outpouching and arranged to facilitate retention of the endovascular member relative to the outpouching, the at least one retention arm having a proximal end and terminating in a distal end having a blunt configuration, the proximal end connected to and extending from the rim;
   wherein the endovascular member and the at least one retention arm are configured to be delivered together to the outpouching.

2. The medical apparatus according to claim 1, wherein the at least one retention arm defines a generally linear configuration.

3. The medical apparatus according to claim 1 further comprising a hydrogel disposed about the endovascular member.

4. The medical apparatus according to claim 3, wherein the hydrogel is radiopaque.

5. The medical apparatus according to claim 1, in combination with:
   a first microcatheter; and
   a delivery member disposed within the first microcatheter, the delivery member coupled to the endovascular member, the delivery member movable within the first microcatheter from an initial condition to a deployed condition to deploy the endovascular member and the at least one retention arm within the outpouching.

6. The medical apparatus according to claim 5, wherein the endovascular member is detachably connected to the delivery member such that a segment of the delivery member remains connected to the endovascular member following detachment, the endovascular member and attached at least one retention arm are detachable from the delivery member after delivery to the outpouching.

7. The medical apparatus according to claim 6, wherein at least one separate embolic coil is deliverable independently through a second microcatheter and into the outpouching.

8. The medical apparatus according to claim 7 further comprising a matrix of embolic coils deliverable through the second microcatheter, the matrix adapted to form shapes of suitable geometry to fill the outpouching.

9. The medical apparatus of claim 6, in combination with at least one separate intrasaccular aneurysm embolic member that can be delivered independently into the outpouching before the endovascular member is detached from the delivery member.

10. The medical apparatus according to claim 5, wherein the delivery member defines a channel therethrough.

11. The medical apparatus according to claim 10, wherein the channel is open on both ends and is configured to deliver at least one separate embolic device independently through the channel of the delivery member and into the outpouching.

12. The medical apparatus according to claim 11, wherein the channel is configured to deliver at least one coil therethrough and into the outpouching.

13. The medical apparatus according to claim 11 further comprising at least one coil configured for insertion into the channel.

14. The medical apparatus according to claim 5, in combination with a second microcatheter.

15. The medical apparatus according to claim 5, wherein the delivery member comprises a hypotube.

16. The medical apparatus according to claim 15, wherein the hypotube is open on both ends and is configured to deliver at least one embolic device therethrough.

17. The medical apparatus according to claim 5 wherein the at least one retention arm extends away from the delivery member in a radial direction.

18. The medical apparatus according to claim 17, wherein the proximal end of the at least one retention arm is spaced from the delivery member by a first distance, and the distal end of the at least one retention arm is spaced from the delivery member by a second distance greater than the first distance.

19. The medical apparatus according to claim 1, wherein the distal end of the at least one retention arm is external of the endovascular member and the proximal end of the least one retention arm is distal of a proximalmost surface of the endovascular member.

20. The medical apparatus according to claim 1, wherein an intermediate portion of the at least one retention arm extends distally and is spaced from the endovascular member.

21. The medical apparatus according to claim 1, wherein the endovascular member is impregnated with adhered hydrogel in a sufficient amount to secure the endovascular member into the outpouching.

22. The medical apparatus according to claim 21, wherein the adhered hydrogel is radio-opaque.

23. The medical apparatus according to claim 1, wherein the endovascular member includes an opening extending therethrough to permit introduction of an embolic material.

24. The medical apparatus according to claim 1, wherein the flat disc is expandable within the outpouching.

25. The medical apparatus according to claim 1, wherein the distal end of the at least one retention arm is devoid of bulbs.

26. The medical apparatus according to claim 1 further comprising a delivery member coupled to the endovascular member before insertion.

27. The medical apparatus according to claim 26, wherein the delivery member includes an open-ended channel.

28. The medical apparatus according to claim 27, wherein the open-ended channel is configured to deliver at least one additional device therethrough.

29. The medical apparatus according to claim 28, wherein the open-ended channel is configured to deliver at least one separate embolic coil therethrough and into the outpouching.

30. The medical apparatus according to claim 28 further comprising at least one separate embolic coil configured for insertion into the open-ended channel.

31. The medical apparatus according to claim 28, wherein the delivery member is detachable from the endovascular member.

32. The medical apparatus according to claim 28, wherein the delivery member includes a detachment zone adjacent to the endovascular member.

33. The medical apparatus according to claim 32, wherein the delivery member includes a distal segment permanently attached to the endovascular member such that the distal segment detaches from a proximal segment of the delivery member upon activation of a detachment mechanism.

34. A medical apparatus for ameliorating an outpouching, comprising:
an endovascular member dimensioned for insertion into the outpouching, wherein the endovascular member includes:
a mesh, and the endovascular member defining flat distalmost and proximalmost surfaces coplanar with the mesh, whereby the endovascular member is configured as a flat disc defining a rim; and
at least one retention arm permanently connected to the endovascular member such that the at least one retention arm extends radially outward from the rim, the at least one retention arm having a proximal end extending from the distalmost surface and a distal end having a blunt configuration, the at least one retention arm configured to engage a wall of the outpouching and arranged to facilitate retention of the endovascular member relative to the outpouching, the endovascular member and the at least one retention arm are adhered together prior to insertion into a body of a patient.

35. The medical apparatus of claim 34, wherein the at least one retention arm is positioned adjacent a separate embolic coil subsequently inserted into the outpouching.

36. The medical apparatus according to claim 34, wherein the distal end of the at least one retention arm is devoid of bulbs.

37. A medical apparatus for ameliorating an outpouching, comprising:
an endovascular member dimensioned to be positioned relative to a neck of the outpouching, wherein the endovascular member includes:
a mesh, the endovascular member defining flat distalmost and proximalmost surfaces coplanar with the mesh, whereby the endovascular member is configured as a flat disc defining a rim; and
at least one retention arm extending radially outward from the rim such that the at least one retention arm extends away from a centerpoint of the flat disc in a radial direction, the at least one retention arm having a proximal end extending from a peripheral portion of the distalmost surface and a distal end having a blunt configuration, the at least one retention arm configured to engage a wall of the outpouching and arranged to facilitate retention of the endovascular member relative to the outpouching.

38. The medical apparatus of claim 37, wherein the at least one retention arm is permanently connected to the endovascular member before insertion.

39. The medical apparatus according to claim 38, further including a delivery member defining a channel capable of delivering at least one coil therethrough.

40. The medical apparatus according to claim 39, wherein the at least one retention arm is generally linear in shape.

41. The medical apparatus according to claim 39, wherein the flat disc further comprises peripheral lips.

42. The medical apparatus according to claim 39, wherein the flat disc is self-expanding upon removal of an external constraint.

43. The medical apparatus according to claim 42, wherein the self-expansion occurs over one second or less of time.

44. The medical apparatus according to claim 42, wherein the self-expansion occurs over more than 1 second of time.

45. The medical apparatus according to claim 39, wherein the at least one retention arm extends away from the delivery member in a radial direction.

46. The medical apparatus according to claim 39, wherein the distal end of the at least one retention arm is devoid of bulbs.

* * * * *